(12) United States Patent
Kinnunen

(10) Patent No.: US 6,222,184 B1
(45) Date of Patent: Apr. 24, 2001

(54) DEVICE FOR MEASURING THE SURFACE PRESSURE

(75) Inventor: Paavo Kinnunen, Espoo (FI)

(73) Assignee: Kibron Inc. Oy, Helsinki (FI)

( * ) Notice: Subject to any disclaimer, the term of this patent is extended or adjusted under 35 U.S.C. 154(b) by 0 days.

(21) Appl. No.: 09/254,715

(22) PCT Filed: Sep. 12, 1997

(86) PCT No.: PCT/FI97/00542

§ 371 Date: Mar. 12, 1999

§ 102(e) Date: Mar. 12, 1999

(87) PCT Pub. No.: WO98/11421

PCT Pub. Date: Mar. 19, 1998

(30) Foreign Application Priority Data

Sep. 13, 1996 (FI) ........................................ 963612

(51) Int. Cl.[7] ...................................................... B05D 1/20
(52) U.S. Cl. .................. 250/231.19; 118/402; 427/434.4
(58) Field of Search ....................... 250/231.19; 73/64.44; 427/434.3; 118/402

(56) References Cited

U.S. PATENT DOCUMENTS 4,413,506  11/1983  Abraham et al. .
5,143,745 * 9/1992  Maganas et al. ........................ 428/8

FOREIGN PATENT DOCUMENTS 2304812  8/1974 (DE) .

OTHER PUBLICATIONS

Derwent's abstract, No. 93–3590022/45, Nov. 7, 1992 (Abstract of SU 1774230) See PCT search rpt.

Patent Abstract of Japan No. 1-212336, vol. 13, No. 520. See PCT search rpt.

* cited by examiner

Primary Examiner—Stephone B. Allen
(74) Attorney, Agent, or Firm—Armstrong, Westerman, Hattori, McLeland & Naughton, LLP

(57) ABSTRACT

The object of the invention is a device for measuring the surface pressure of a film formed at the interface of a liquid and gaseous phase, the device comprising a detector means and a sensor means. The detector means comprises a light source and a position-sensitive detector, the active surface of which is situated in the light beam of the light source, and the sensor means comprises a sensor which can be brought into contact with the film to be measured, and a shading means which, in correspondence with the force applied to the sensor by the film, moves in the light beam between the active surface of the detector and the light source.

4 Claims, 2 Drawing Sheets

DEVICE FOR MEASURING THE SURFACE PRESSURE

The object of the present invention is a device for measuring the surface pressure of a film, a so-called Langmuir film, formed at the boundary surface between the phases of a liquid and gaseous material.

Some organic compounds, such as surface-active compounds of liquid crystal type, for example phosphoglycerol and treitol derivatives substituted by long-chained aliphatic hydrocarbon chains, fatty acids and their derivatives, form monomolecular layers at a liquid and gas interface. Such films are called Langmuir-films and, transferred onto a solid substrate, Langmuir-Blodgett—, that is LB-films. Such films can be used, for example, in electronics, optics, and in photo-chemical applications, for example in sensors, microcircuits, photocells etc. In the original publication by Irwin Langmuir (Langmuir, I. (1917), J. Am. Chem. Soc. 39, 1848) the principles have been presented according to which compounds arrange themselves to form monomolecular surface films. Various methods for the preparation and study of monomolecular surface films have been discussed extensively in the monography by George Gaines (Gaines, G. L., Jr (1966): Insoluble Monolayers at Liquid-Gas Interfaces, Interscience Publishers, John Wiley and Sons Inc., New York 1966).

In short, the technique of manufacturing films according to Langmuir-Blodgett is based on allowing a film-forming surface-active material to orient itself in the boundary surface between two different phases, for example that of a liquid, such as water, glycerol etc. and a gas, such as air, argon etc., whereby the hydrophilic part of the molecule orients itself into the liquid and the hydrophobic part away from the liquid. An organic substance dissolved in a suitable organic solvent or solvent mixture, such as chloroform or cyclohexane, is spread as a monomolecular layer over the surface of the liquid in a trough and the solvent is evaporated. By means of a barrier resting on the trough edges in contact with the liquid surface, the area of the liquid-gas-interface available for the film is restricted, thus allowing for an increase or reduction of the total surface area of the monomolecular surface film.

By means of the barrier it is thus possible to regulate the surface tension of the film, which is inversely proportional to the surface pressure $\pi$. When a supporting body functioning as a substrate or carrier is moved through the boundary surface, preferably at constant speed, the film is transferred as a monomolecular layer onto the support, the hydrophobic part toward the support, when the body is moved through the boundary surface in the direction from gas to liquid, and the hydrophilic part toward the support, when the direction is the opposite. The thickness of an individual film layer is primarily dependent on the organic compound used for the manufacture of the film and especially on the length of the acid chains contained therein. Usually it is of the magnitude of 20–30 Å. By moving the barrier, the surface pressure of the film is kept constant during coating. This requires that the surface pressure is continuously and accurately monitored.

The surface pressure is measured, for example, by measuring the force applied to a sensor in the film by means of a sensitive balance. For example, a thin platinum plate (Wilhelmy plate) can be used as a sensor, which typically is of the size 1×2 cm and which is placed in the liquid/gas interface, in contact with the film layer. The changes in the surface pressure are evidenced as changes in the quantity or mass of liquid (water) adhered to the plate. When the surface pressure of the liquid increases, the quantity of water adhered to the plate is linearly reduced, and vice versa. The surface of the sensor is wetted by the influence of the surface pressure, which is evidenced as an increase in weight of the sensor plate or in the load applied to the sensor. The force applied to the sensor by the surface pressure in turn makes the sensor move in the vertical direction. This force can be measured using, for example, a commercial microbalance (Sartorius, Cahn, etc.).

Nowadays, also a so-called LVDT-sensor is used for measuring the surface pressure. The LVDT (linear voltage displacement transducer) is comprised of an iron core moving within a solenoid in a sleeve, whereby the position of the iron core within the solenoid affects the output voltage of the solenoid. A disadvantage is that the core is of a magnetizable material, and of necessity heavy. Thus the mass of the core limits the force (mass) that can be detected by the LVDT when it is most sensitive. The measurement sensitivity obtainable with this device is thus not satisfactory. Microbalances, on the other hand, are very expensive and require much space. In some measurement applications it is, in addition, necessary to use a protecting gas (for example argon) to stabilize the film. Such an application is, for example, film fluorescence microscopy, wherein, under the influence of exciting light, oxygen molecules can react with fluorescent groups in the lipid film, thus modifying them photochemically and quenching the fluorescence. On the other hand, the sample space of the fluorescence microscope is so small that it is not possible to use, for example, a microbalance and protecting gas during measurement.

According to the invention a device has been invented, which allows for the measurement of the surface pressure with a very high degree of accuracy, by using a position-sensitive detector together with a light source for measuring the displacement of the sensor.

Thus the object of the invention is a device for measuring the surface pressure of a film formed at the interface of a liquid and gaseous phase, the device comprising a detector means and a sensor means, characterized in that the detector means comprises a light source and a position-sensitive detector, the active surface of which is situated in the light beam of the light source, and the sensor means comprises a sensor which can be brought into contact with the film to be measured, and a shading means which, in correspondence with the force applied to the sensor by the film, moves in the light beam between the active surface of the detector and the light source.

The device according to the invention thus comprises a detector means and a sensor means. The detector means is comprised of a position-sensitive detector and a light source mounted in a housing or carried by a supporting structure or frame. The position-sensitive detector and the light source are arranged with respect to each other so that the light beam from the light source hits the active surface of the position-sensitive detector. The position- sensitive detector (PSD-detector) is preferably a one-dimensional position-sensitive detector. It comprises a silicon substrate and a layer structure formed thereon. The outermost layer is resistive, that is an active P-layer. The incident light which falls on the active P-layer is converted to an electrical charge which is proportional to the light energy. Ibis charge is driven through the P-layer to electrodes connected to the layer. As the resistivity of the layer is constant, a photo current is obtained at the electrodes, which is inversely proportional to the distance between the incident light spot and the electrodes. The most sensitive PSD:s can detect the position of a light spot on the light sensitive surface with a degree of accuracy of even 0.1 µm.

As the light source, a suitable commercially available light emitting diode, for example IR diode PDI-E802 (manuf. Phototronic Detectors, Inc. USA) can be used.

The sensor means of the device according to the invention comprises a sensor which can be brought into contact with the film to be measured, as well as a shading means functionally connected thereto. According to the invention, the film surface pressure, that is the load applied to the sensor, is transmitted to the shading means, which in turn moves in the light beam between the light source and the detector. The term "functionally connected" means here that the force applied to the sensor by the surface pressure of the film to be measured, which is proportional to the surface pressure, is linearly transmitted to the shading means, to effect a displacement of the shading means.

For example a platinum plate known for the purpose, or a NiCr-wire may be used as the sensor to be placed in the film to be measured. A NiCr-wire is especially advantageous as it is able to measure the surface pressure without hysteresis typical for Pt. Under the influence of the surface pressure, the sensor moves in the vertical direction, which movement is transmitted to the shading means. The shading means is of such dimensions and shape that it shades at least part of the light sensitive surface in a suitable manner. The shading means can thus be shaped, for example, as a rectangle or square, the largest dimension or surface of which is substantially perpendicular to the light beam and substantially parallel to the active surface of the position-sensitive detector. As a result of the movement of the shading means, the lit area on the light sensitive surface of the detector changes, and thus also the output currents of the detector. From the output current, the force needed to displace the sensor, that is the surface pressure, can be calculated. Due to the high sensitivity of the PSD, also very small loads on the sensor, and movements, can be registered with the PSD.

Various solutions can be used for transmitting the movement of the sensor to the shading means. One of the most simple embodiments of the invention is such, wherein the sensor is suspended, for example over a sensor shaft, from a spring, for example a sensitive leaf spring, which is arranged substantially horisontally and one end of which is attached in a suitable manner to a support, e.g. the housing or the frame. The other free end of the spring, suitably bent or folded to form a substantially vertically extending end portion, forms the shading means. According to another embodiment, the sensor and shading means respectively, are fastened each to one end of its own arm which arms in turn are connected to a pivot point or pin transmitting the movement from one arm to the other. For this purpose, for example, a torsion wire can be used, which e.g. is mounted to extend between its two ends attached to the housing or frame of the device, and which is sensitive to movement and transmits the same.

In the following reference is made to the appended drawing, which in a schematic manner illustrates an embodiment of a device according to the invention.

Figure 1:
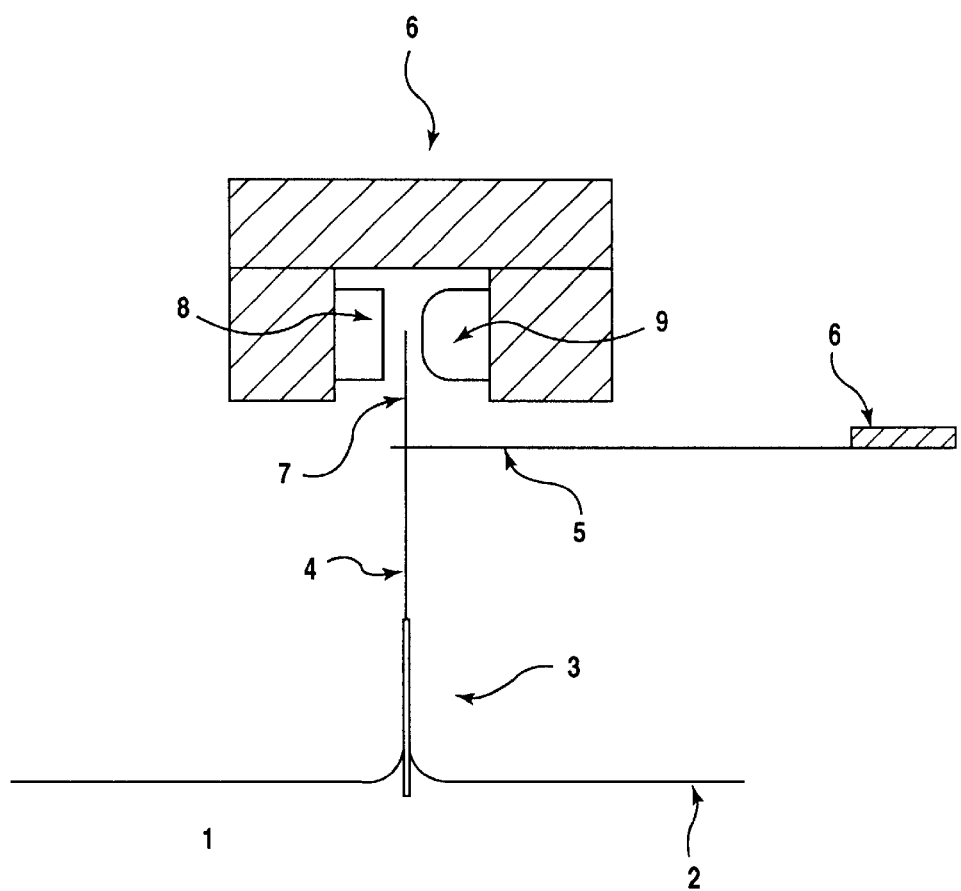
FIG. 1 shows in a schematic manner one embodiment of the device according to the invention.

In the FIG. 1 of the drawing, the lower liquid phase is marked with the reference number 1 and the monomolecular film resting thereon with reference number 2, the surface pressure of which is to be measured. Into the film 2 a platelike platinum sensor 3 is immersed in the vertical direction, to which sensor a stiff wire or shaft 4 is attached, which in turn is supported by a sensitive leaf spring 5. One end of the spring 5 is in a suitable manner attached to a support 6. The other free end 7 of the spring is bent vertically upward and forms a tongue-like shading means. The shading means is positioned in the light beam from a light emitting diode 9 aligned to direct the light to the sensitive surface of a position-sensitive detector 8. When the surface pressure of the film changes, the quantity of liquid adhered to the sensor 3 changes, and thus also the force or load on the sensor. The force generated displaces the sensor vertically upward or downward to a degree corresponding to the surface pressure. This displacement movement is transmitted over the wire 4 and spring 5 to the shading means 7, which correspondingly moves in the light field. The displacement of the shade changes the lit surface area of the detector 8, which in turn generates a change in the output current of the detector corresponding to the displacement (or surface pressure).

Figure 2:
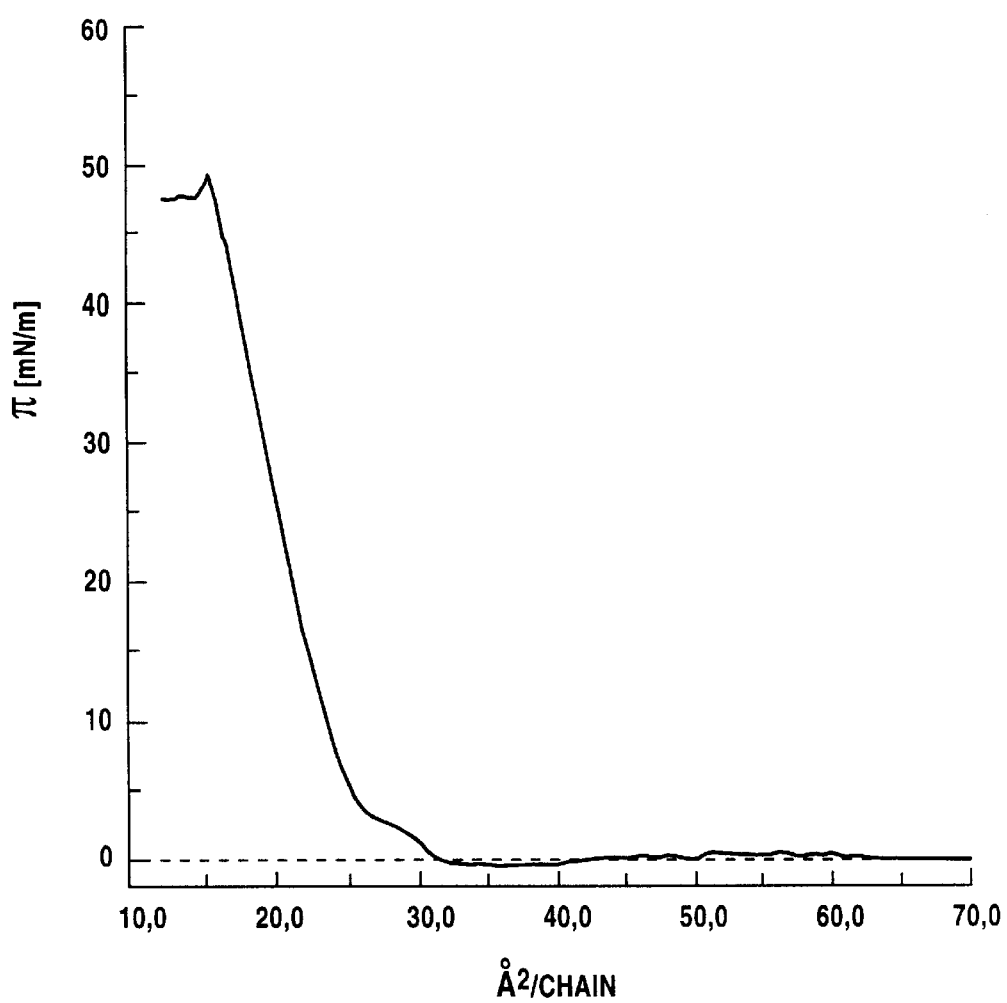
FIG. 2 shows the surface pressure as a function of the surface area, a compression isotherm, measured with the device according to the invention.

The reliability and linearity of the measurement results have been tested using, in place of a sensor, weights of different magnitude attached to the leaf spring to simulate the load exerted by the surface pressure. It has been observed that the device functions linearly in the range of approximately 40 mg to 90 mg, which corresponds to the conditions encountered in practice in surface pressure measurements. Typically, the increase in mass by pure water, using a NiCr-wire with a circumference of 1.73 mm, is 11.8 mg, which corresponds to a surface tension of water of 71.8 mN m$^{-1}$ at the upper limit of the measuring range. On the other hand, from the compression isotherm of FIG. 2 it can be seen that the device measures the surface pressure with very high resolution.

What is claimed is:

1. Device for measuring the surface pressure of a film formed at the interface of a liquid and gaseous phase, the device comprising a detector means and a sensor means, characterized in that the detector means comprises:

a light source and a position-sensitive detector, the active surface of which is situated in the light beam of the light source, and the sensor means comprises:

a sensor which can be brought into contact with the film to be measured; and a shading means which, in correspondence with the force applied to the sensor by the film, moves in the light beam between the active surface of the detector and the light source, wherein the position-sensitive detector is a PSD-detector, and the sensor or a shaft portion connected thereto is attached to or suspended from a spring mounted to a support, the free end of which forms the shading means.

2. The device according to claim 1, characterized in that the light source is a light emitting diode.

3. The device according to claim 1, characterized in that the sensor and the shading means, respectively, are supported each by its own arm which arms are functionally connected and pivotable with respect to a pivot point.

4. The device according to claim 3, characterized in that the pivot point is formed by a torsion wire arranged to extend within the housing or frame of the device.

* * * * *